United States Patent
Harvey et al.

(10) Patent No.: US 9,994,498 B2
(45) Date of Patent: Jun. 12, 2018

(54) RENEWABLE HIGH DENSITY TURBINE AND DIESEL FUELS FROM SESQUITERPENES

(71) Applicant: The United States of America as represented by the Secretary of the Navy, Washington, DC (US)

(72) Inventors: Benjamin G. Harvey, Ridgecrest, CA (US); Heather A. Meylemans, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 1054 days.

(21) Appl. No.: 13/676,541

(22) Filed: Nov. 14, 2012

(65) Prior Publication Data

US 2015/0031927 A1     Jan. 29, 2015
US 2015/0315097 A9     Nov. 5, 2015

Related U.S. Application Data

(63) Continuation-in-part of application No. 12/511,796, filed on Jul. 29, 2009, now Pat. No. 8,395,007.

(60) Provisional application No. 61/562,681, filed on Nov. 22, 2011.

(51) Int. Cl.
| | |
|---|---|
| C07C 5/13 | (2006.01) |
| C10L 1/04 | (2006.01) |
| C10G 1/00 | (2006.01) |
| C07C 7/00 | (2006.01) |
| C07C 5/25 | (2006.01) |
| C10L 1/08 | (2006.01) |
| C10G 3/00 | (2006.01) |

(52) U.S. Cl.
CPC .............. *C07C 5/13* (2013.01); *C07C 5/2506* (2013.01); *C07C 7/00* (2013.01); *C10G 1/00* (2013.01); *C10G 3/42* (2013.01); *C10G 3/44* (2013.01); *C10G 3/45* (2013.01); *C10G 3/50* (2013.01); *C10L 1/04* (2013.01); *C10L 1/08* (2013.01); *C10G 2300/1014* (2013.01); *C10G 2400/04* (2013.01); *C10G 2400/08* (2013.01); *Y02E 50/13* (2013.01); *Y02P 30/20* (2015.11); *Y02T 50/678* (2013.01)

(58) Field of Classification Search
CPC ......... Y02E 50/00; Y02E 50/13; Y02E 50/30; C10L 2290/54
See application file for complete search history.

(56) References Cited

U.S. PATENT DOCUMENTS

| | | | |
|---|---|---|---|
| 775,963 A * | 11/1904 | Houdry ................ | G03B 23/048 353/116 |
| 9,109,175 B2 * | 8/2015 | Lee ........................ | C10L 1/04 |
| 2008/0092829 A1 | 4/2008 | Renninger et al. | |
| 2009/0020089 A1 | 1/2009 | Ryder et al. | |
| 2009/0020090 A1 | 1/2009 | Ryder et al. | |
| 2009/0272119 A1 | 11/2009 | Ryder | |

(Continued)

*Primary Examiner* — Ellen M McAvoy
*Assistant Examiner* — Ming Cheung Po
(74) *Attorney, Agent, or Firm* — Charlene A. Haley

(57) ABSTRACT

A fuel and method for conversion of sesquiterpenes to high density fuels. The sesquiterpenes can be either extracted from plants or specifically produced by bioengineered organisms from waste biomass. This approach allows for the synthesis of high performance renewable fuels.

22 Claims, 1 Drawing Sheet

(56) References Cited

U.S. PATENT DOCUMENTS

2009/0272352 A1 11/2009 Ryder
2012/0116138 A1* 5/2012 Goodall .................. C10G 45/08
585/357

* cited by examiner

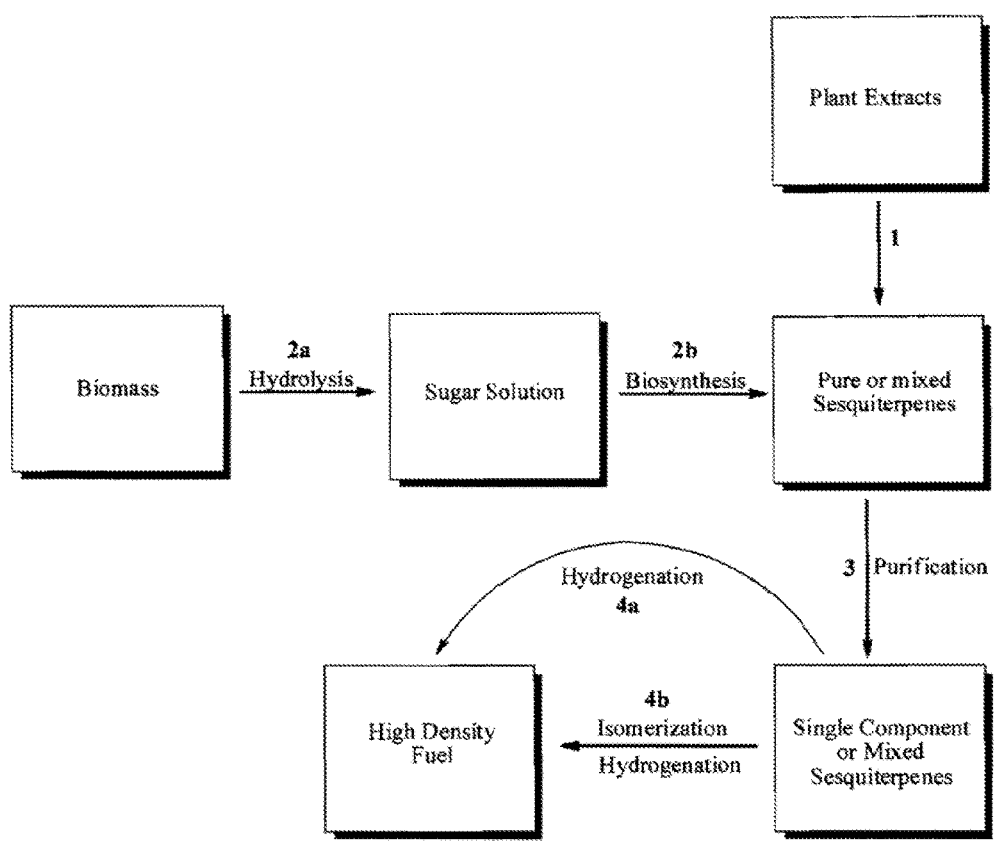

RENEWABLE HIGH DENSITY TURBINE AND DIESEL FUELS FROM SESQUITERPENES

CROSS-REFERENCE TO RELATED APPLICATIONS

This is a non-provisional patent application of, claiming the benefit of, parent application Ser. No. 61/562,681 filed on Nov. 22, 2011, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the conversion of sesquiterpenes to high density fuels.

BRIEF DESCRIPTION OF THE DRAWINGS

FIG. 1 is a block diagram illustrating the steps to produce high density biofuels from sesquiterpenes, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to the conversion of sesquiterpenes to high density fuels.

The biosynthesis of farnesene and use as a standalone diesel/jet fuel or component of same is covered in the following USPTO applications: 20090272352, 20090272119, 20090020090, 20090020089, and 20080092829. Farnesane, the reduced form of farnesene, is a linear sesquiterpene of relatively low density (0.766 g/mL).

High density fuels have applications in a variety of Navy platforms including jet aircraft, ships, missiles, and UAVs. The fuels developed herein will help to meet Navy goals focused on the use of renewable and sustainable fuels while providing improved performance over conventional, petroleum-based fuels.

Embodiments of this invention describe the conversion of sesquiterpenes to high density fuels. The sesquiterpenes can be either extracted from plants or specifically produced by bioengineered organisms from waste biomass. This approach allows for the synthesis of high performance renewable fuels.

Embodiments of the invention detail processes for conversion of sesquiterpenes to high density fuel mixtures. Aspects of the process include hydrogenation of the sesquiterpenes to improve stability of the fuels as well as selective isomerization of the sesquiterpenes to improve density, net heat of combustion, low temperature viscosity, and cetane number. The isomerization process can be carried out with heterogeneous catalysts at moderate temperatures and requires no solvent. Thus, embodiments of the invention provide a route for the sustainable production of renewable ultra-performance fuels.

The general procedure for synthesizing high density sesquiterpene fuels is as follows:

1. A pure sesquiterpene or mixture of sesquiterpenes are either extracted from plant sources (e.g. clove oil) or
2. a) A biomass source (including lignocellulosic, cellulosic, or hemicellulosic feedstocks) is hydrolyzed to produce a sugar solution
   b) The sugar solution is fermented to a sesquiterpene or mixture of sesquiterpenes by a bioengineered organism.
3. The hydrocarbons are purified by solvent extraction, pervaporation, membrane separation, or distillation.
4. Pure sesquiterpenes or mixtures are then:
   a) Directly hydrogenated and distilled to yield a liquid fuel or
   b) Isomerized with heterogeneous acidic catalysts to produce a pure compound or complex mixture of hydrocarbons which is then hydrogenated and distilled to yield a liquid fuel.

Process:

1. A pure sesquiterpene or mixture of sesquiterpenes is isolated from a plant source. This can be accomplished by steam distillation, solvent extraction, or pyrolysis, among other techniques.

2a. In an alternate approach, biomass can be hydrolyzed to produce a sugar solution. This step can be accomplished by physical, chemical, or enzymatic methods, or any combination thereof.

2b. The sugar solution is used as a food source for bioengineered organisms that produce sesquiterpenes in either a batch or continuous mode.

3. Regardless of the source, the sesquiterpenes can be upgraded through techniques including fractional distillation, chemical treatments, and extractions to produce a suitably pure hydrocarbon feedstock composed of either a single sesquiterpene or complex mixture of sesquiterpenes. In the case of the biosynthesized sesquiterpenes (2b), the major impurity is water which can be effectively removed by both membrane separation techniques as well as by distillation.

4a) Sesquiterpenes are directly hydrogenated to produce a high density fuel. Catalysts based on Ni, Pd, Pt, Cu, and Ru can be utilized under moderate hydrogen pressures.

4b) To improve specific fuel properties such as viscosity, net heat of combustion, density, and cetane number, sesquiterpenes can be readily isomerized with heterogeneous acid catalysts including, but not limited to; Nafion, Amberlyst, Montmorillonite K-10, zeolites and supported polyphosphoric acid. Sesquiterpenes can also be effectively isomerized with Lewis acids and mineral acids. After isomerization, these sesquiterpenes can be hydrogenated as in 4a. Pure sesquiterpenes or defined mixtures of sesquiterpenes can be isolated by fractional distillation to generate fuels with specific properties. FIG. 1 is a block diagram overview showing the steps of the embodiments of the invention therein.

Example 1 (High Catalyst Loading)

50 mL of caryophyllene (technical grade) is combined with 500 mg of Nation SAC-13 in a flask. The mixture is vigorously stirred and heated to 100° C. overnight. The pale yellow solution is decanted, hydrogenated at 50 psig $H_2$ with 50 mg $PtO_2$ as catalyst. The resulting mixture is filtered and vacuum distilled to yield a colorless fuel mixture containing saturated hydrocarbons derived from seven main isomers including α-neoclovene, clovene, and α-panasinsene (see Schematic 1).

Schematic 1. Products resulting from the acid-catalyzed isomerization of β-caryophyllene. Numbers under the structures represent the weight percentage of each molecule. The first number results from low catalyst loading, while the number in parentheses results from high catalyst loading as described in the process.

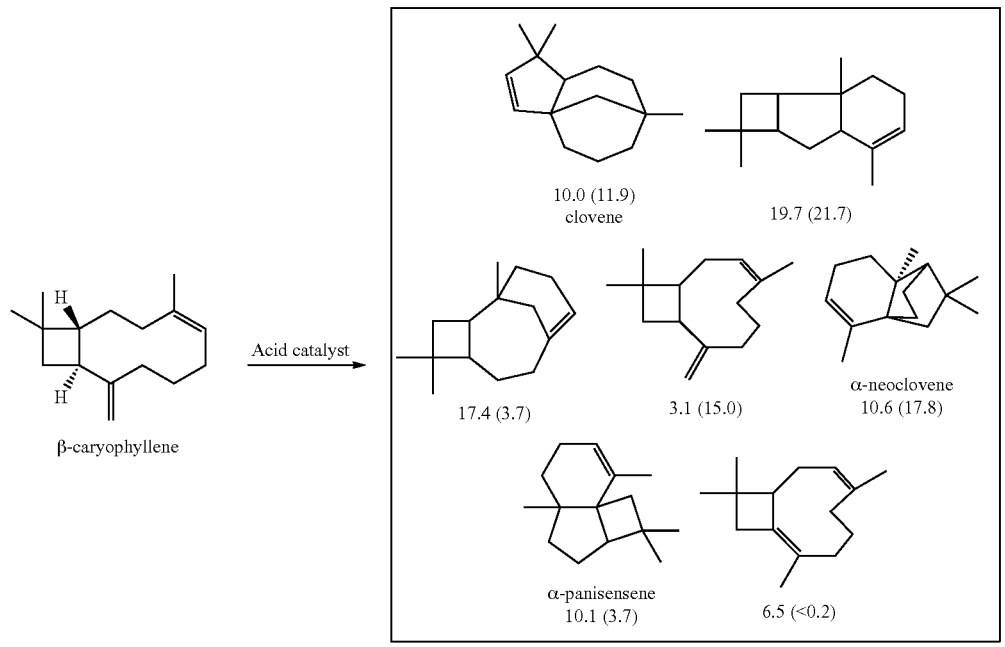

Example 2 (Low Catalyst Loading)

500 mL of caryophyllene is combined with 2 g of Nation SAC-13 in a flask and subjected to the same conditions as in Example 1. A significantly different product distribution results (see Schematic 1).

Example 3

175 mL of valencene (Scheme 3) biosynthesized from sucrose is hydrogenated at 50 psig $H_2$ with 100 mg $PtO_2$ as catalyst. After hydrogenation the catalyst flocculates and the catalyst is separated by decantation. The properties of this fuel mixture are listed in Table 1.

Example 4

175 mL of premnaspirodiene (Scheme 3) biosynthesized from sucrose is hydrogenated as in Example 3. The properties are listed in Table 1.

Example 5

175 mL of commercial caryophyllene (technical grade) is hydrogenated as in Example 3. The properties are listed in Table 1.

Example 6

5 g of valencene biosynthesized from sucrose are combined with 0.1 g of Nafion SAC-13 and the mixture is stirred and heated to 100° C. for 16 h. The solution is decanted to yield a mixture of isomers.

Example 7

5 g of premnaspirodiene biosynthesized from sucrose is isomerized as described in Example 6.

TABLE 1

Key Properties of Sesquiterpene Fuels.
Table 1. Key Properties of Sesquiterpene Fuels

| Sesquiterpene | Density (g/mL) | NHOC (btu/gal) | 40° C. Viscosity (cSt) | −20° C. Viscosity (cSt) | Ignition Delay (ms) | Derived Cetane No. |
|---|---|---|---|---|---|---|
| Valencane | 0.879 | 135,386 | 4.417 | 50.24 | 10.562 | 23.26 |
| Caryophyllane | 0.85 | 132,790 | 4.067 | 60.47 | 9.75 | 24.52 |
| Premnaspirodiane | 0.882 | 135,564 | 3.812 | 42.91 | 7.779 | 28.65 |
| HDCL-8 | 0.90 | 137,800 | 53.58 | NM | 13.173 | 20.23 |

TABLE 1-continued

Key Properties of Sesquiterpene Fuels.
Table 1. Key Properties of Sesquiterpene Fuels

| Sesquiterpene | Density (g/mL) | NHOC (btu/gal) | 40° C. Viscosity (cSt) | −20° C. Viscosity (cSt) | Ignition Delay (ms) | Derived Cetane No. |
|---|---|---|---|---|---|---|
| HDCL-9  | 0.90 | 137,100 | 5.07 | 61.96 | 6.549 | 32.53 |
| HDCL-10 | 0.92 | 140,900 | NM   | NM    | NM    | NM    |

Note:
HDCL-8 is the fuel generated from caryophyllene with high catalyst loading, HDCL-9 is the fuel generated with low catalyst loading. The density and net heat of combustion of HDCL-10 has been calculated based on a distillate cut containing primarily high-density components (i.e. clovene/neoclovene and assuming a density of 0.92 g/mL).

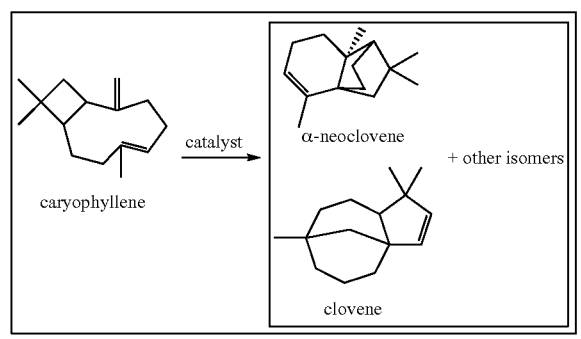

Scheme 2.
Isomerization of caryophyllene with a heterogeneous acid catalyst.

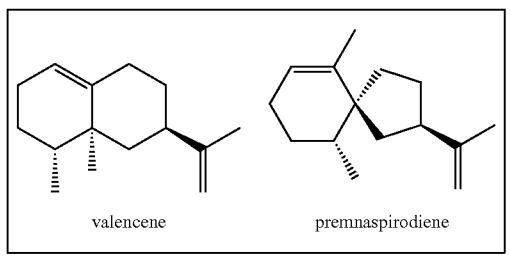

Scheme 3. Structures of valencene and premnaspirodiene.

Embodiments of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes, converting the single component or mixed sesquiterpenes by either, directly hydrogenating the single component or mixed sesquiterpenes with at least one hydrogenation catalyst under hydrogen pressure, or isomerizing either with or without a solvent, the single component or mixed sesquiterpenes with at least one heterogeneous acid catalyst to produce isomers and hydrogenating the isomers with at least one hydrogenation catalyst under hydrogen pressure, and distilling either the hydrogenated single component or mixed sesquiterpenes or the hydrogenated isomers to produce high density fuels.

Another aspect of the invention generally relates to the production and blends of fuels. In embodiments, the pure and/or mixed sesquiterpenes are selected from the group consisting of valencene, premnaspirodiene, caryophyllene, humulene, clovene, neoclovene, panasinsene, thujopsene, longifolene, cubebene, zizaene, santalene, longipinene, isomers of the above sesquiterpenes, other cyclic terpenes, and any mixtures thereof. In embodiments, the single component or mixed sesquiterpenes are selected from the group consisting of caryophyllene, valencene, premnaspirodiene, or any mixture thereof. In embodiments, the isomers are at least one isomer selected from the group consisting of α-neoclovene, clovene, or any mixture thereof. In embodiments, the hydrogenating catalyst having at least one metal selected from the group consisting of Ni, Cu, Pd, Pt, $PtO_2$, Ru and the reaction is conducted without a solvent.

In embodiments, the heterogeneous acid catalyst are selected from the group consisting of at least one of Nafion (perfluorinated sulfonic acid resins), Amberlyst (cross-linked sulfonic acid resins), Montmorillonite K-10, zeolites, polyphosphoric acids, cation exchange resins. Lewis acid catalysts, supported Bronsted acid catalysts, mineral acids including $H_2SO_4$ and $H_3PO_4$, and any mixtures thereof. In embodiments, the plant extracts are selected from the group consisting of clove oil or any essential oil having significant quantities of cyclic sesquiterpenes, and mixtures of said oils. In embodiments, the biomass includes at least one of sucrose, glucose, fructose, cellobiose, other reducing sugars, cellulose, and hemicelluloses in any proportion.

Another aspect of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes producing a first set of fuels, or converting the single component or mixed sesquiterpenes by isomerizing either with or without a solvent, the single component or mixed sesquiterpenes with at least one heterogeneous acid catalyst to produce isomers, and distilling the isomers producing a second set of fuels. All blends of fuels are incorporated into all aspects of the invention.

Yet other aspects of the invention generally relate to a first set of fuels produced from the methods above. Still yet other aspects of the invention generally relate to a second set of fuels produced from the methods above.

In embodiments, the fuels are pure sesquiterpanes or prepared by selective fractional distillation of sesquiterpane mixtures (density>0.90 g/mL, NHOC>137,000 btu/gal). In other embodiments, the diesel fuels are pure sesquiterpanes or generated by selective fractional distillation of sesquiterpane mixtures (cetane number>30). In yet other embodiments, the diesel fuels are generated by blending sesquiterpane mixtures with known cetane enhancers or antioxidants for fuels. In embodiments, the fuels generated by blending sesquiterpene fuels with petroleum-based fuels including JP-10, RJ-4, JP-8, JP-5, F-76, Diesel #2, Jet A, and any renewable fuel.

In embodiments, the high density missile/turbine fuels are blends of cyclic sesquiterpanes with JP-10 in a desired proportion. In embodiments, the high density jet fuels are blends of cyclic sesquiterpanes with jet fuels including JP-5, JP-8, and Jet A. In embodiments, the high density diesel fuels are blends of cyclic sesquiterpanes with petroleum-derived diesel fuel. In embodiments, the high density jet/diesel fuels are blends of cyclic sesquiterpanes with fuels generated by ethylene oligomerization. In embodiments, the high density jet/diesel fuels are blends of cyclic sesquiterpanes with fuels generated by butene oligomerization. In embodiments, the high density jet/diesel fuels are blends of cyclic sesquiterpenes with fuels generated by hexene oligomerization. In embodiments, the high density jet/diesel fuels are blends of cyclic sesquiterpanes with diesel fuels produced from natural gas.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for manufacturing jet and diesel fuels, comprising:
    providing sesquiterpenes isolated from plant extracts and/or biosynthesized from biomass;
    purifying said sesquiterpenes to produce purified sesquiterpenes;
    converting said purified sesquiterpenes to non-aromatic multicyclic sesquiterpenes by isomerization with at least one heterogeneous acid catalyst;
    hydrogenating said non-aromatic multicyclic sesquiterpenes isomers to produce hydrogenated multicyclic sesquiterpenes; and
    distilling said hydrogenated non-aromatic multicyclic sesquiterpenes to produce high density fuels, wherein said fuels having a minimum density of 0.85 g/mL and a minimum net heat of combustion of 132,700 btu/gal.

2. The method according to claim 1, wherein said sesquiterpenes are selected from the group consisting of valencene, premnaspirodiene, caryophyllene, humulene, clovene, neoclovene, panasinsene, thujopsene, longifolene, cubebene, zizaene, santalene, longipinene, isomers of sesquiterpenes, and any mixtures thereof.

3. The method according to claim 1, wherein said sesquiterpenes are selected from the group consisting of caryophyllene, valencene, premnaspirodiene, or any mixture thereof.

4. The method according to claim 1, wherein said non-aromatic multicyclic sesquiterpene isomers are at least one isomer selected from the group consisting of α-neoclovene, clovene, or any mixture thereof.

5. The method according to claim 1, wherein said hydrogenating catalyst having at least one metal selected from the group consisting of Ni, Cu, Pd, Pt, $PtO_2$, Ru and the reaction is conducted without a solvent.

6. The method according to claim 1, wherein said heterogeneous acid catalyst are selected from the group consisting of at least one of Nafion (perfluorinated sulfonic acid resins), Amberlyst (cross-linked sulfonic acid resins), Montmorillonite K-10, polyphosphoric acids, cation exchange resins, Lewis acid catalysts, supported Bronsted acid catalysts, mineral acids including $H_2SO_4$ and $H_3PO_4$, and any mixtures thereof.

7. The method according to claim 1, wherein said plant extracts are selected from the group consisting of clove oil or any essential oil having significant quantities of cyclic sesquiterpenes, and mixtures of said oils.

8. The method according to claim 1, wherein said biomass includes at least one of sucrose, glucose, fructose, cellobiose, other reducing sugars, cellulose, and hemicelluloses in any proportion.

9. The method according to claim 1, wherein said high density fuels are pure sesquiterpanes or prepared by selective fractional distillation of hydrogenated multicyclic sesquiterpane mixtures with density >0.90 g/mL and net heat of combustion >137,000 Btu/gal).

10. The method according to claim 1, wherein said high density diesel fuels are pure sesquiterpanes or generated by selective fractional distillation of hydrogenated multicyclic sesquiterpane mixtures with cetane number >30.

11. The method according to claim 1, wherein said high density diesel fuels are generated by blending hydrogenated multicyclic sesquiterpane mixtures with known cetane enhancers.

12. The method according to claim 1, wherein said high density fuels are generated by blending hydrogenated multicyclic sesquiterpene fuels with petroleum-based fuels including JP-10, RJ-4, JP-8, JP-5, F-76, Diesel #2, Jet A, and any renewable fuel.

13. The method according to claim 1, wherein said high density missile/turbine fuels are blends of hydrogenated multicyclic sesquiterpanes with JP-10 in a desired proportion.

14. The method according to claim 1, wherein said high density jet fuels are blends of hydrogenated multicyclic sesquiterpanes with jet fuels including JP-5, JP-8, and Jet A.

15. The method according to claim 1, wherein said high density diesel fuels are blends of hydrogenated multicyclic sesquiterpanes with petroleum-derived diesel fuel.

16. The method according to claim 1, wherein said high density jet/diesel fuels are blends of hydrogenated multicyclic sesquiterpanes with fuels generated by ethylene oligomerization.

17. The method according to claim 1, wherein said high density jet/diesel fuels are blends of hydrogenated multicyclic sesquiterpanes with fuels generated by butene oligomerization.

18. The method according to claim 1, wherein said high density jet/diesel fuels are blends of hydrogenated multicyclic sesquiterpanes with fuels generated by hexene oligomerization.

19. The method according to claim 1, wherein said high density jet/diesel fuels are blends of hydrogenated multicyclic sesquiterpanes with diesel fuels produced from natural gas.

20. High density fuels produced from the methods of claim 1.

21. A method for manufacturing jet and diesel fuels, comprising:
  providing sesquiterpenes isolated from plant extracts and/or biosynthesized from biomass;
  purifying said sesquiterpenes to purified sesquiterpenes;
  converting said purified sesquiterpenes to non-aromatic multicyclic sesquiterpenes with at least one heterogeneous acid catalyst to produce non-aromatic multicyclic sesquiterpene isomers; and
  distilling said non-aromatic multicyclic sesquiterpene isomers producing a set of fuels.

22. A set of fuels produced from the methods of claim 21.

\* \* \* \* \*